United States Patent [19]
De Boer et al.

[11] Patent Number: 5,814,709
[45] Date of Patent: Sep. 29, 1998

[54] PROCESS FOR HYDROGENATION ON CONJUGATAED DIENE POLYMERS AND CATALYST COMPOSITION SUITABLE FOR USE THEREIN

[75] Inventors: Eric Johannes Maria De Boer; Bart Hessen; Adriaan Albert Van Der Huizen; Wouter De Jong; Adrianus Johannes Van Der Linden; Bart Johan Ruisch; Lodewijk Schoon; Heleen Johanna Augusta De Smet; Frederik Hendrik Van Der Steen; Hubertus Cornelis Thomas Lucianes Van Strien; Alan Villena; Judith Johanna Berendina Walhof, all of CM Amsterdam, Netherlands

[73] Assignee: Shell Oil Company, Houston, Tex.

[21] Appl. No.: 831,631

[22] Filed: Apr. 9, 1997

[30] Foreign Application Priority Data

Apr. 12, 1996 [EP] European Pat. Off. ............. 96302600

[51] Int. Cl.$^6$ .................................................. C08F 8/04
[52] U.S. Cl. ...................... 525/337; 502/129; 525/332.8; 525/332.9; 525/333.1; 525/333.2; 525/339
[58] Field of Search ............................. 502/129; 525/337, 525/339

[56] References Cited

U.S. PATENT DOCUMENTS

| | | | |
|---|---|---|---|
| 3,663,635 | 5/1972 | Lassau et al. | 260/666 P |
| 3,766,300 | 10/1973 | De La Mare | 260/879 |
| 3,898,208 | 8/1975 | Krause | 260/85.1 |
| 4,501,857 | 2/1985 | Kishimoto et al. | 525/338 |
| 5,541,272 | 7/1996 | Kishimoto et al. | 525/338 |

FOREIGN PATENT DOCUMENTS

| | | |
|---|---|---|
| 0434469 A2 | 12/1990 | European Pat. Off. . |
| 0460725 B1 | 5/1991 | European Pat. Off. . |
| 0471415 A1 | 8/1991 | European Pat. Off. . |
| 0532099 A1 | 9/1992 | European Pat. Off. . |
| 0544304 A1 | 11/1992 | European Pat. Off. . |
| 0545844 A1 | 12/1992 | European Pat. Off. . |
| 0549063 A2 | 12/1992 | European Pat. Off. . |
| 0601953 A1 | 2/1994 | European Pat. Off. . |
| 1289-805-A | 11/1989 | Japan . |
| 2159819 | 4/1985 | United Kingdom . |
| 95/25136 | 3/1994 | WIPO . |

OTHER PUBLICATIONS

"Mechanism of Acetylene Polymerization on the $NiCL_2$–$NaBH_4$ System in Alcohols," by N.S. Gorkova, F.S. Diachkovski, P.E. Matkovski, Chemical Abstracts, vol. 90, No. 4, Jan. 22, 1979, pp. 774–77.

Primary Examiner—Bernard Lipman
Attorney, Agent, or Firm—Donald F. Haas

[57] ABSTRACT

The invention provides a catalyst composition suitable for hydrogenation of polymers containing ethylenic unsaturation, which comprise:

(a) a titanium compound of the formula,

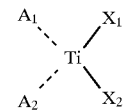

wherein $A_1$ and $A_2$ are the same or different and each represents a substituted or unsubstituted cyclopentadienyl or indenyl group, wherein $X_1$ and $X_2$ are the same or different and each represents hydrogen, halogen, a lower alkyl or lower alkoxy, optionally substituted phenyl or phenoxy, or aralkyl having from 7 to 10 carbon atoms, or phenylalkoxy having from 7 to 10 carbon atoms, carboxyl, carbonyl, a —$CH_2P(Phenyl)_2$, —$CH_2 Si(lower alkyl)_3$, or —$P(phenyl)_2$ group.

(b) an alkalimetal hydride, added as such or prepared in situ in the polymer solution from the alkalimetal terminated living polymer and/or from additionally added alkalimetal alkyl and hydrogen, the molar ratio of the alkalimetal:titanium in the polymer solution during hydrogenation being at least 2:1;

(c) a borium compound

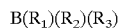

wherein the symbols $R_1$, $R_2$ and $R_3$ may be the same or different and each may represent hydrogen, halogen, lower alkyl or lower alkoxy, or phenyl optionally substituted by up to five substituents selected from halogen and lower alkyl, or benzyl having an optionally substituted phenyl ring as specified hereinbefore or wherein two of the symbols R may form together a monocyclic or bicyclic system which on its own may carry one or more substituents. A process for hydrogenation of polymers containing ehylenic unsaturation using these catalyst compositions is also described.

14 Claims, No Drawings

5,814,709

PROCESS FOR HYDROGENATION ON CONJUGATAED DIENE POLYMERS AND CATALYST COMPOSITION SUITABLE FOR USE THEREIN

FIELD OF THE INVENTION

The invention relates to a process for the hydrogenation of conjugated diene polymers and catalysts usable therefor. More in particular, the invention relates to a process for the hydrogenation of polymers and copolymers of conjugated diene polymers using a hydrogenation catalyst comprising at least a titanium compound and an alkali metal compound.

BACKGROUND OF THE INVENTION

Polymers of conjugated dienes such as 1,3-butadiene and isoprene and the copolymers of these dienes with vinylaromatic monomers, e.g. with styrene, are widely used in industry as elastomers. These polymers contain double bonds in their chain, which permit their vulcanization, but whose presence causes a low resistance to ageing and oxidation. Some block copolymers of conjugated dienes and vinylaromatic hydrocarbons are used without vulcanization as thermoplastic elastomers, as transparent impact-resistant resins, or as modifiers or compatibilizers of polystyrene and polyolefin resins. However these copolymers have a low resistance to ageing and oxidation by atmospheric oxygen and by ozone, due to the presence of double bonds in their chain. Hence the use of these copolymers in applications requiring exposure to the external environment is limited.

The resistance to oxidation by oxygen and ozone, and, in general, the resistance to ageing, may be considerably improved by hydrogenating these polymers to obtain total or partial saturation of the double bonds. Numerous processes have been proposed for the hydrogenation of polymers which contain olefinic double bonds bonds but they generally fall within one of two groups: those which use supported heterogeneous catalysts and those which use homogeneous catalysts of the Ziegler type or organometallic compounds of rhodium and titanium.

Numerous catalysts are known for the hydrogenation of compounds containing unsaturated double bonds, catalysts which may be classified into two groups: (1) heterogeneous catalysts, generally consisting of a metal such as Ni, Pd, Pt, Ru, etc., optionally deposited on a support such as carbon, silica, alumina, calcium carbonate, etc.; and (2) homogeneous catalysts such as (a) Ziegler catalysts consisting of a combination of an organic salt of Ni, Co, Fe, Cr, etc. and a reducing agent such as an organoaluminum compound and (b) single component organometallic compounds of Ru, Rh, Ti, La, etc.

Heterogeneous catalysts are widely used in industry but compared with the homogeneous catalyst they are less active and, in order to carry out the desired hydrogenation with these heterogeneous catalysts, large quantities of catalyst are needed and the reaction must be carried out at relatively high pressures and temperatures. The homogeneous catalysts are generally more active. A small amount of catalyst is sufficient and the hydrogenation reaction can be carried out under milder pressure and temperature conditions.

In the processes using supported heterogeneous catalysts, the polymer to be hydrogenated is first dissolved in a suitable solvent and then contacted with hydrogen in the presence of the heterogeneous catalyst. The contact of the reactants with the catalyst is difficult due to the relatively high viscosity of the polymer solution, steric hindrances within the polymer chain, and the high adsorption of the polymer which, once hydrogenated, tends to remain on the surface of the catalyst and interfere with the access to the active centres of the nonhydrogenated polymer. To achieve complete hydrogenation of the double bonds, large quantities of catalyst and severe reaction conditions are required. Usually this causes decomposition and gelification of the polymer. Furthermore, in the hydrogenation of copolymers of conjugated dienes with vinylaromatic hydrocarbons, the aromatic nuclei are also hydrogenated and it is difficult to effect a selective hydrogenation of the double bonds of the polydiene units. Likewise, physical separation of the catalyst from the solution of hydrogenated polymer is extremely difficult and, in some cases, a complete elimination is impossible due to the strong adsorption of the polymer on the heterogeneous catalyst.

In processes using Ziegler-type catalytic systems, the reaction takes place substantially in a homogeneous medium and the hydrogenation of copolymers may be carried out under mild pressure and temperature conditions. Moreover, by adequately selecting the conditions of hydrogenation it is possible to selectively hydrogenate the double bonds of the poly(conjugated diene) blocks without hydrogenating the aromatic rings of the poly(vinylaromatic hydrocarbon) blocks. Nevertheless the elimination of the catalyst residues from the reaction product—which is absolutely necessary because these residues have an unfavourable effect on the stability of the hydrogenated polymers—is a complicated and costly step.

Other processes using other homogeneous catalysts, e.g. the rhodium compounds described in U.S. Pat. No. 3,898,208 and in the Japanese patent JP 01.289,805 have the disadvantage of the high cost of the rhodium catalysts.

It is known that hydrogenation catalysts in which one of the components is a derivative of cyclopenta-dienyltitanium (U.S. Pat. No. 4,501,857) are used—necessarily in the presence of organolithium compounds—for the hydrogenation of the olefinic double bonds of the polymers of conjugated dienes. European Patent application 0,460,725 describes the use of a similar catalyst system for the hydrogenation of polymers that had been synthesised by means of an organolithium compound and which have been terminated by the addition of hydrogen, the presence of the lithium hydride formed in the final reaction being necessary in this case to generate an active catalyst. The examples of both patents use the compound $Cp_2TiCl_2$.

To obtain more economical hydrogenation processes, present-day industry feels the need of having homogeneous catalyst available which are stable, more effective than those currently known, and active in concentrations that are sufficiently low so as to be able to avoid the costly step of elimination of catalyst residues from the hydrogenated polymer. Therefore it will be appreciated that one object of the present invention is to provide an improved catalyst composition to be used for said process.

SUMMARY OF THE INVENTION

As a result of extensive research and experimentation there has been surprisingly found such a catalyst and process aimed at. Accordingly, the present invention relates to catalyst compositions for hydrogenation of polymers containing ethylenic unsaturation, which comprises at least:
(a) a titanium compound of the formula

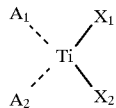

wherein $A_1$ and $A_2$ are the same or different and each represents a substituted or unsubstituted cyclopentadienyl or indenyl group.

wherein $X_1$ and $X_2$ are the same or different and each represents hydrogen, halogen and preferably chlorine, a lower alkyl or lower alkoxy, optionally substituted phenyl or phenoxy, or aralkyl having from 7 to 10 carbon atoms and preferably benzyl, or phenylalkoxy group having from 7 to 10 carbon atoms, carboxyl, carbonyl, a —$CH_2P(Phenyl)_2$, —$CH_2 Si(lower\ alkyl)_3$ or —$P(phenyl)_2$ group.

(b) an alkalimetal hydride, added as such or prepared in situ in the polymer solution from the alkalimetal terminated living polymer and/or from additionally added alkalimetal alkyl and hydrogen, the molar ratio of the alkalimetal:titanium being at least 2:1;

(c) a borium compound

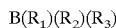

wherein the symbols $R_1$, $R_2$ and $R_3$ may be the same or different and each may represent hydrogen, halogen, lower alkyl or lower alkoxy, or phenyl optionally substituted by up to five substituents selected from halogen and lower alkyl, or benzyl having an optionally substituted phenyl ring as specified hereinbefore or wherein two of the symbols R may form together a monocyclic or bicyclic system which on its own may carry one or more substituents. Examples of such optionally substituted cyclic systems are optionally substituted cycloboranes.

With the term "lower alkyl" or "lower alkoxy" as used throughout this specification, is meant that these groups contain from 1 to 4 carbon atoms. Preferred substituents of possible phenyl groups represented by $R_1$, $R_2$ and $R_3$, are fluoro, chlorine or methyl.

It will be appreciated that another aspect of the present invention is formed by a process for the hydrogenation of polymers containing ethylenic unsaturation (carbon—carbon double bonds) by bringing a polymer solution in intensive contact with hydrogen in the presence of at least the catalyst composition of this invention which is formed of components (a), (b) and (c).

DETAILED DESCRIPTION OF THE INVENTION

The catalyst composition of this invention must contain the titanium compound described above (component (a)). As described, this is a cyclopentadienyl or indenyl (or both) titanium compound.

$A_1$ and $A_2$ may represent unsubstituted cyclopentadienyl or indenyl groups or substituted cyclopentadienyl or indenyl groups. The groups $A_1$ and $A_2$ are optionally substituted by halogen, phenyl which optionally may bear one or more of the same or different substituents, and/or lower alkyl, alkoxy, phenoxy, phenylalkoxy, benzyl and/or a bulky substituent containing one or more hetero atoms such as tri(lower alkyl)silyl, —$NPh_2$, —NHPh, —$BPh_2$, or —$B(OPh)_2$. When one or more, and preferably one or two, of the substituents represent phenyl, they may optionally be substituted by one or more substituents selected from lower alkyl, halogen, preferably fluoro or chloro, and lower alkoxy. Examples thereof are para-tert butylphenyl, pentafluorophenyl, dichlorophenyl, 3,5 di(t-butyl)4-methoxy phenyl, and trifluorophenyl.

$X_1$ and $X_2$ are preferably selected from halogen and in particular chlorine, methyl, methoxy, ethyl, ethoxy, ispropoxy, isopropyl, tert butyl, tert butoxy, phenyl, phenoxy, and benzyl. Most preferably $X_1$ and $X_2$ are both chlorine.

The most preferred titanium compounds are bis (cyclopentadienyl) titanium dichloride, bis(1-indenyl) titanium dichloride, bis(1-indenyl) titanium diphenoxide, bis (cyclopentadienyl) titanium diphenoxide, bis (cyclopentadienyl) titanium dimethoxide, bis(indenyl) titanium dimethoxide, or derivatives thereof which are substituted on their indenyl or cyclopentadienyl rings by one or more and preferably one or two methyl groups, methoxy groups, para-tert butyl phenyl groups, penta fluorophenyl groups, trifluoro phenyl groups, dichloro phenyl groups; or 3-5-(t-butyl)-4-methoxyphenyl groups.

The titanium compound is used in amounts of from 5 to 100 mg per kg of conjugated diene polymer to be hydrogenated and preferably in amounts in the range of from 20 to 60 mg/kg of conjugated diene polymer to be hydrogenated.

Lithium hydride is preferably used as alkalimetal hydride (component (b)). The polymerisation initiator to be used for the initiating living polymer of at least one conjugated diene and the optional additional amounts of alkalimetal compound to form additional alkalimetal hydride are preferably organolithium compounds. They are preferably selected from methyllithium, ethyllithium, p-tolyl lithium, xylylithium, 1,4-dilithiobutane, alkylene dilithium, and the reaction product of butyl lithium and divinyl benzene. Particularly preferred are n-butyl lithium, sec butyl lithium, tert-butyl lithium, and phenyllithium. Most preferred are tert butyllithium, sec-butyllithium, and n-butyllithium. The molar ratio of lithium hydride to titanium is preferably at least 6 and more preferably in the range of from 6 to 25.

Suitably the molar ratio of the borium:titanium during hydrogenation is at least 1/10. More in particular, the borium:titanium molar ratio during hydrogenation is in the range of from 1/10 to 10 and preferably in the range of from 1/2 to 2 and most preferably in the range of from 0.9 to 1.1.

Polymers with a high degree of hydrogenation can be obtained according to the process of the present invention. The catalyst system has been surprisingly found to show a significantly higher activity, resulting in a higher hydrogenation rate of the starting polymer as compared with prior art homogeneous Ti catalyst hydrogenation processes. Moreover this catalyst can be dosed more accurately and shows an excellent reproductivity.

As the catalyst system in the present process can be applied in a significantly lower concentration, its concentration in the final hydrogenated product is much lower. The hydrogenation process can be performed at partial hydrogen pressures in the range of from 1 to 50 bar and preferably from 1–35 bar.

According to a more preferred embodiment of the hydrogenation process of the present invention one or more promoters (d) may be present in addition to the beforementioned catalyst components (a), (b) and (c). Said promoters (d) can be selected from polar ketone compounds, hydroxy group containing ketone compounds, aldehyde compounds, ester compounds, lactone compounds, lactam compounds, and epoxy compounds. Of the beforementioned promoters, especially preferred are ketone compounds hydroxy group-containing ketone compounds, aldehyde compounds, ester compounds, and epoxy compounds.

Specific examples of preferred ketone compounds include acetone, diethyl ketone, di-n-propyl ketone, di-i-propyl ketone, di-sec-butyl ketone, di-t-butyl ketone, methyl ethyl ketone, i-propyl methyl ketone, i-butyl methyl ketone, 2-pentanone, 3-hexanone, 3-decanone, diacetyl, acetophenone, 4'-methoxy acetophenone, 4'-methyl acetophenone, propiophenone, benzophenone, 4-methoxy benzophenone, 4,4'-dimethoxy benzophenone, benzyl phenyl ketone, benzil acetone, benzoyl acetone, cyclopentanone, cyclohexanone, 4-methyl cyclohexanone, 1,2-cyclohexane dione, cycloheptanone, acetyl acetone.

Hydroxy group-containing ketone compounds are defined as compounds having both a hydroxy group and a ketone carbonyl group in the molecule. Specific examples of preferred compounds are hydroxyacetone, acetoin, 4-hydroxy-2-butanone, 3-hydroxy-3-methyl-2-butanone, 5-hydroxy-2-butanone, diacetone alcohol, 4-(p-hydroxyphenyl)-2-butanone, 2-hydroxyacetophenone, 2'-hydroxyacetophenone, 3'-hydroxyacetophenone, 4'-hydroxyacetophenone, 4'-hydroxy-3'-methoxyacetophenone, 2-hydroxyphenyl ethyl ketone, 4'-hydroxypropiophenone, 2',4'-dihydroxyacetophenone, 2,',5'-dihydroxyacetophenone, 2',6'-dihydroxyacetophenone, 3',5'-dihydroxyacetophenone, 2',3',4'-dihydroxyacetophenone, 2-hydroxybenzophenone, 4-hydroxybenzophenone, 2-hydroxy-4-methoxybenzophenone, 2-hydroxy-4-n-octyloxybenzophenone, 2,2'-dihydroxybenzophenone, 2,4-dihydroxybenzophenone, 4,4'-dihydroxybenzophenone, 2,2'-dihydroxy-4-methoxybenzophenone, 2,,4'-trihydroxybenzophenone, benzoin.

Either aliphatic or aromatic aldehyde compounds can be used. The aliphatic group in aliphatic aldehyde compounds may be saturated or unsaturated and linear or branched. Given as examples of preferable aldehyde compounds are formaldehyde, acetaldehyde, propionaldehyde, n-butylaldehyde, i-butylaldehyde, n-valeraldehyde, i-valeraldehyde, pivalaldehyde, n-capronaldehyde, 2-ethylhexyladehyde, n-heptaldehyde, n-caprylaldehyde, pelargonaldehyde, n-caprinaldehyde, n-undecylaldehyde, laurylaldehyde, tridecylaldehyde, myristylaldehyde, pentadecylaldehyde, palmitylaldehyde, margarylaldehyde, stearylaldehyde, glyoxal, succinaldehyde, benzaldehyde, o-tolualdehyde, m-tolualdehyde, p-tolualdehyde, α-naphthaldehyde, β-naphthaldehyde, phenylacetnaphthaldehyde.

Examples of ester compounds are esters formed by a monobasic acid, e.g. formic acid, acetic acid, propionic acid, butyric acid, capronic acid, pelargonic acid, lauric acid, palmitic acid, stearic acid, isostearic acid, cyclohexylpropionic acid, cyclohexyl-capronic acid, benzoic acid, phenylbutyric acid, etc., a dibasic acid, e.g., oxalic acid, maleic acid, malonic acid, fumaric acid, succinic acid, glutaric acid, adipic acid, pimelic acid, suberic acid, sebacic acid, itaconic acid, phthalic acid, isophthalic acid, terephthalic acid, azelaic acid, etc.; or a polybasic acid, e.g., 1,2,3-propanetricarboxylic acid, 1,3,5-n-pentanetricarboxylic acid, etc., and an alcohol, e.g., methyl alcohol, ethyl alcohol, isopropyl alcohol, n-butyl alcohol, sec-butyl alcohol, tert-butyl alcohol, amyl alcohol, hexyl alcohol, octyl alcohol, phenol, cresol, 1,3-butanediol, 1,4-butanediol, piniacol, pentaerythritol, etc.

Specific examples of lactone compounds are β-propiolactone, γ-butyrolactone, ε-caprolactone, Δα,β-crotonlactone, Δβ,γ-crotonlactone, coumarin, phthalide, α-pyrone, sydonone, fluoran.

Given as specific examples of lactam compounds are β-propiolactam, 2-pyrrolidone, 2-piperidone, ε-caprolactam, n-heptanelactam, 8-octanelactam, 9-nonanelactam, 10-decanelactam, 2-quinolone, 1-isoquinolone, oxinedole, iso-indigo, isatin, hydantoin, quinolidinone.

Specific examples of preferred epoxy compounds include 1,3-butadiene monoxide, 1,3-butadiene dioxide, 1,2-butylene oxide, 2,3-butylene oxide, cyclohexene oxide, 1,2-epoxy cyclododecane, 1,2-epoxy decane, 1,2-epoxy eicosane, 1,2-epoxy heptane, 1,2-epoxy hexadecane, 1,2-epoxy octadecane, 1,2-epoxy octane, ethylene glycol diglycidyl ether, 1,2-epoxy heptane, 1,2-epoxy tetradecane, hexamethylene oxide, isobutylene oxide, 1,7-octadiene diepoxide, 2-phenylpropylene oxide, propylene oxide, trans-stilbene oxide, styrene oxide epoxylated 1,2-polybutadiene, epoxylated linseed oil, glycidyl methyl ether, glyciyl n-butyl ether, glycidyl allyl ether, glycidyl methacrylate, glycidyl acrylate.

Polymers

Included in the olefinically unsaturated polymers to be hydrogenated by the catalyst composition of the present invention are all polymers containing olefinically carbon—carbon unsaturated double bonds in the polymer main chain or side chains. Typical examples are conjugated diene polymers and random, block, or graft polymers of conjugated dienes and olefins.

Included in the above conjugated diene polymers are conjugated diene homopolymers and copolymers produced from conjugated dienes or from at least one conjugated diene and at least one olefin copolymerisable with the conjugated diene. Given as typical examples of conjugated dienes used for the production of these conjugated diene polymers are conjugated dienes having 4–12 carbon atoms. Specific examples are 1,3-butadiene, isoprene, 2,3-dimethyl-1,3-butadiene, 1,3-pentadiene, 2-methyl-1,3-pentadiene, 1,3-pentadiene, 1,3-hexadiene, 4,5-diethyl-1,3-octadiene, 3-butyl-1,3-octadiene, chloroprene, and the like.

From the aspect of manufacturing elastomers having superior characteristics and industrial advantages, 1,3-butadiene and isoprene are particularly preferable. Elastomers, such as polybutadiene, polyisoprene, and butadiene/isoprene copolymers are especially preferred polymer materials used in the present invention. There are no specific limitations as to the micro-structures of the polymers. All these polymers are suitable materials in the application of the hydrogenation using the catalyst composition of the present invention.

The above-mentioned copolymers produced from at least one conjugated diene and at least one olefin copolymerisable with the conjugated diene are also suitable polymer materials to which the hydrogenation using the catalyst composition of the present invention is applied. The above-described conjugated diene monomers can be used for the manufacture of these types of copolymer. Any olefins copolymerisable with these conjugated dienes are usable for the manufacture of the copolymer, with vinyl-substituted aromatic hydrocarbons being particularly preferred.

Copolymers of conjugated dienes and vinyl-substituted aromatic hydrocarbons are of particular importance for the production of industrially useful and valuable elastomers or thermoplastic elastomers. Given as specific examples of vinyl-substituted aromatic hydrocarbons used in the manufacture of this type of copolymer are styrene, α-methylstyrene, p-methylstyrene, divinylbenzene, 1,1-diphenylethylene, N,N-dimethyl-p-aminoethylstyrene, N,N-diethyl-p-aminoethylstyrene, vinylpyridine. Of these, styrene and a-methylstyrene are particularly preferable. Specific copolymers providing industrially valuable hydrogenated copolymers are butadiene/styrene copolymer, isoprene/styrene copolymer, butadiene/α-methylstyrene copolymer.

These copolymers include random copolymers in which monomers are randomly distributed throughout the polymers, progressively reducing block copolymers, complete block copolymers, and graft copolymers. Preferred polymers include butadiene-styrene block copolymer, isoprene-styrene block copolymers or butadiene/isoprene-styrene block copolymer of linear or radial, multiarmed shape.

In order to manufacture industrially useful thermoplastic elastomers, the amount of vinyl-substituted aromatic hydrocarbons is preferably in the range of from 15 to 45% by weight. A content of vinyl bonds in the conjugated diene units of 10% or more of the total conjugated diene units is desirable for obtaining hydrogenated polymers with superior characteristics.

Included also in polymers which can be used in the hydrogenating process using the catalyst composition of the present invention are those of linear type, as well as branched type or radial or star type, produced by coupling using a coupling agent, all having a weight average molecular weight, generally, of 1,000–1,000,000.

It will be appreciated that the hereinbefore specified polyketone compounds, polyaldehyde compounds, ester compounds, and polyepoxy compounds can be used as coupling agents. These coupling agents can be used as both coupling agents and component (d) of the catalyst composition of the present invention. This ensures an economical advantage of the polymer hydrogenation using the catalyst composition of the present invention.

Also included in polymers to be hydrogenated according to the present invention are those having terminals modified with polar groups after the living anionic polymerisation or by other means. Hydroxy groups, carboxyl groups, ester groups, isocyanate groups, urethane groups, amide groups, urea groups, and thiourethane groups may be used as the polar groups.

Beside the above-mentioned polymers, any polymers manufactured by any polymerisation methods, e.g., anionic polymerisation, cationic polymerisation, coordination polymerisation, radical polymerisation, solution polymerisation, emulsion polymerisation, or the like, can be used in the present invention. In addition, cyclic olefin polymers manufactured by ring-opening polymerisation using a methathesis catalyst, such as molybdenum or tungsten are included in polymers having olefenically unsaturated bonds.

Process

In the hydrogenation reaction using the catalyst composition of the present invention, the olefinically unsaturated polymers may be hydrogenated in a condition where they are dissolved in a hydrocarbon solvent or the olefinically unsaturated polymers may be produced by polymerisation in a hydrocarbon solvent and may be successively hydrogenated.

Hydrocarbon solvents used in the hydrogenation reaction may be aliphatic hydrocarbons, e.g., pentane, hexane, heptane, octane, etc.; alicyclic hydrocarbons, e.g., cyclopentane, methyl cyclopentane, cyclohexane, etc., or an aromatic solvent such as toluene. These hydrocarbon solvents may contain 20% by weight or a smaller amount of ethers such as diethyl ether, tetrahydrofuran, dibutyl ether, diethoxypropane, dioxane.

There are no restrictions as to the concentration of polymers in carrying out the hydrogenation reaction of the present invention. Usually, the polymer concentration is 1–30% by weight, and preferably 3–20% by weight. The hydrogenation reaction is effected, after the addition of the hydrogenation catalyst composition under an inert gas atmosphere, e.g., in nitrogen or argon, or under a hydrogen atmosphere, by supplying hydrogen, with or without stirring, while maintaining the temperature of the polymer solution at a specified temperature.

The temperature suitable for the hydrogenation reaction is 0°–150° C. A temperature lower than 0° C. is uneconomical, since at temperatures lower than 0° C., not only the catalyst activity is lowered but also the rate of hydrogenation is retarded. If the temperature is higher than 150° C., on the other hand, not only do the polymers tend to decompose or to gel but also aromatic rings are hydrogenated at the same time leading to a poor hydrogenation selectivity. A more preferable temperature range is 20°–140° C., and particularly preferably 50°–130° C. In the hydrogenation reaction using the catalyst composition of the present invention, the reaction may be carried out at a comparatively higher temperature, resulting in a higher rate of reaction and a higher yield.

The hydrogenation reaction is carried out for a time period of from 1 minute to 3 hours. The reaction time may be shorter when a larger amount of the catalyst composition is used and the pressure is higher.

The invention will now be illustrated by means of the following examples.

EXAMPLES

Example 1

Preparation of hydrogen terminated SBS block copolymer

A 30 liter batch of polystyrene-polybutadiene-polystyrene (SBS) block copolymer of 70,000 molecular weight was prepared by sequential anionic polymerisation using sec-butyllithium as the initiator in a stainless steel reactor. The polymerisation was conducted in cyclohexane to which had been added 140 ppm of diethoxypropane at 18 wt % solids. The 1,2-content of the SBS polymer was 40.4 wt %.

At the end of the polymerisation reaction, the reactor was sparged with hydrogen for 2 hours to terminate the living SBS-Li polymer and produce SBS and LiH. The LiH content of the batch was determined to be 2.2 mmol/liter.

Example 2

Hydrogenation of SBS block copolymer with bis(indenyl) titanium dichloride

A stainless steel reactor was charged with 190 grams of SBS cement prepared as in Example 1. The temperature of the reactor was fixed at 70° C. and the reactor was pressurised to 10 bar of hydrogen to saturate the cement. Meanwhile a suspension of 0.04 mmol of bis(indenyl) titanium dichloride and bis(n-butylcyclopentadienyl) titanium dichloride, respectively, and 0.04 mmol of boriumtrifluoride, tri(pentafluoro-phenyl) borium, and tri (phenyl) borium, respectively, in 10 ml of cyclohexane was prepared.

The catalyst suspension was added to the reactor and the hydrogen pressure was raised to 50 bar. Immediately, a strong exothermic reaction occurred (T=80° C.). The hydrogenation was allowed to run for 3 hours during which period samples were drawn from the reactor and analysed by 1 H NMR to determine the conversion of the olefinic double bonds. The conversions were determined after 15 minutes, one hour and three hours and are listed in Tables 1 and 2.

TABLE 1

Conversion - time relation for bis(n-butylcyclopenta-dienyl) titanium dichloride and borium compounds
Molar ratio Li:Ti = 15:1; molar ratio Ti:B = 1:1

| Time (min) | $BF_3$ | $B(C_6F_5)_3$ | $B(C_6H_5)_3$ | no addition |
|---|---|---|---|---|
| 15 | 95 | 94 | 91 | 93 |
| 60 | 100 | 100 | 99 | 98 |
| 180 | 100 | 100 | 100 | 99 |

TABLE 2

Conversion - time relation for bis(Indenyl) titanium dichloride and borium compounds
Molar ratio Li:Ti = 15:1; molar ratio Ti:B = 1:1

| Time (min) | $BF_3$ | $B(C_6F_5)_3$ | $B(C_6H_5)_3$ | no addition |
|---|---|---|---|---|
| 15 | 82 | 78 | 76 | 72 |
| 60 | 91 | 86 | 82 | 75 |
| 180 | 95 | 91 | 88 | 77 |

We claim:

1. A catalyst composition usable for hydrogenation of polymers containing ethylenic unsaturation, which comprises:
(a) a titanium compound of the formula,

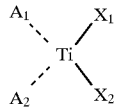

wherein $A_1$ and $A_2$ are the same or different and each represents a substituted or unsubstituted cyclopentadienyl or indenyl group,
wherein $X_1$ and $X_2$ are the same or different and each represents hydrogen, halogen, a lower alkyl or lower alkoxy, optionally substituted phenyl or phenoxy, or aralkyl having from 7 to 10 carbon atoms, or phenylalkoxy having from 7 to 10 carbon atoms, carboxyl, carbonyl, a —$CH_2P(Phenyl)_2$, —$CH_2 Si(lower alkyl)_3$ or —$P(phenyl)_2$ group
(b) an alkalimetal hydride, the molar ratio of the alkali metal:titanium being at least 2:1; and
(c) a borium compound of the formula,

$B(R_1)(R_2)(R_3)$ wherein the symbols $R_1$, $R_2$ and $R_3$ may be the same or different and each may represent hydrogen, halogen, lower alkyl or lower alkoxy, or phenyl optionally substituted by up to five substituents selected from halogen and lower alkyl, or benzyl having an optionally substituted phenyl ring or wherein two of the symbols R may form together a monocyclic or bicyclic system which on its own may carry one or more substituents.

2. A catalyst compositions according to claim 1 characterised in $X_1$ and $X_2$ are selected from chlorine, methyl, methoxy, ethyl, ethoxy, isopropoxy, isopropyl, tert butyl, tert butoxy, phenyl, phenoxy, and benzyl.

3. A catalyst compositions according to claim 2 characterised in that $X_1$ and $X_2$ are both chlorine.

4. A catalyst compositions according to claim 1 characterised in that the borium:titanium molar ratio is in the range of from 1/10 to 10.

5. A catalyst compositions according to claim 4 characterised in that the borium:titanium molar ratio is in the range of from ½ to 2.

6. A catalyst compositions according to claim 5 characterised in that the borium:titanium molar ratio is in the range of from 0.9 to 1.1.

7. A catalyst compositions according to claim 1 characterised in that the alkali metal hydride is lithium hydride.

8. A catalyst composition according to claim 7 characterised in that the molar ratio of lithium hydride to titanium is at least 6.

9. A catalyst composition according to claim 8 characterised in that the molar ratio of lithium hydride to lithium is in the range of from 6 to 25.

10. A catalyst composition according to claim 1 characterised in that it comprises in addition to components (a), (b) and (c), one or more promoters (d), selected from polar ketone compounds, hydroxy group containing ketone compounds, aldehyde compounds, ester compounds, lactone compounds, lactam compounds, and epoxy compounds.

11. A catalyst compositions according to claim 10 characterised in that it comprises a promoter selected from ketone compounds, hydroxy group containing ketone compounds, aldehyde compounds, ester compounds, and epoxy compounds.

12. A catalyst compositions according to claim 10 characterised in that the molar ratio of component (a) to component (d) is in the range of from 10 to ½.

13. A catalyst compositions according to claim 10, characterised in that the molar ratio of component (a) to component (d) is in the range of from 2 to 1.

14. A process for the hydrogenation of polymers containing ethylenic unsaturation, said process comprising bringing a polymer solution in intensive contact with hydrogen in the presence of the catalyst composition of claim 1.

* * * * *